Figure 4:
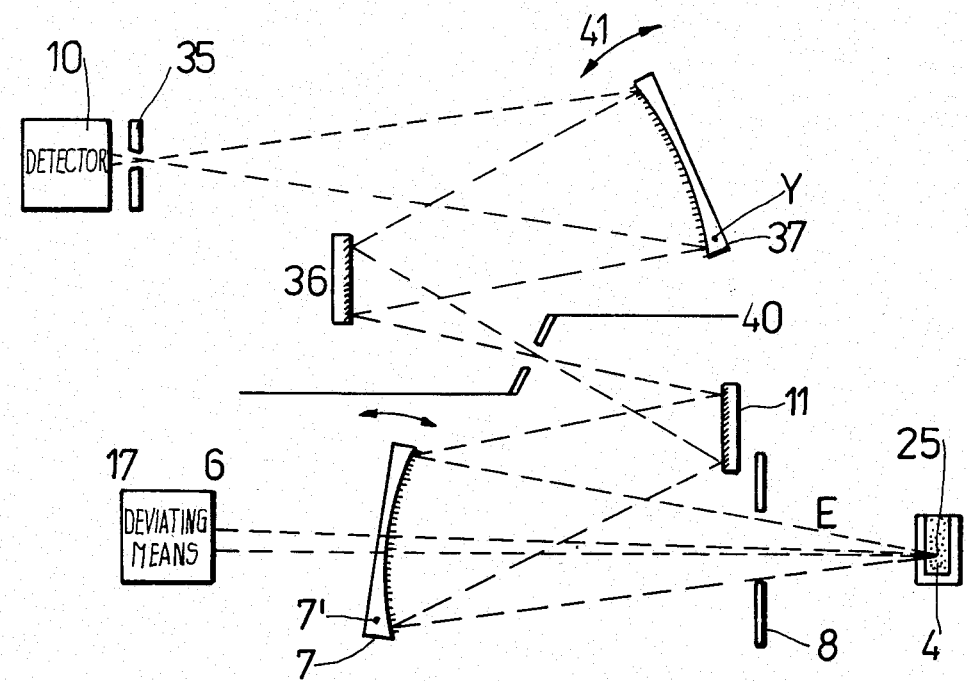

United States Patent [19]

Lucht et al.

[11] Patent Number: 4,490,040

[45] Date of Patent: Dec. 25, 1984

[54] SPECTRALFLUOROMETER ARRANGEMENT

[76] Inventors: Hartmut Lucht, 12, Semnonenweg, 1185 Altglienicke, District of Berlin; Rainer Wendt, 11, Altheiderstrasse, 1199 Berlin; Heinz Drommert, 4, Margaretenstrasse, 1150 Berlin, all of German Democratic Rep.

[21] Appl. No.: 376,757

[22] Filed: May 18, 1982

[30] Foreign Application Priority Data

Jun. 10, 1981 [DD] German Democratic Rep. ... 230692

[51] Int. Cl.³ .............................................. G01N 21/64
[52] U.S. Cl. ................................ 356/318; 250/458.1; 356/73
[58] Field of Search ............... 356/301, 317, 318, 332, 356/334, 73; 250/458.1, 459.1, 461.1, 467.2

[56] References Cited

U.S. PATENT DOCUMENTS

| 3,542,481 | 11/1970 | Slomba | 356/301 X |
| 3,567,322 | 3/1971 | Brehm et al. | 356/332 |
| 3,753,618 | 8/1973 | Haley | 356/334 |
| 4,351,611 | 9/1982 | Leif | 356/318 |

Primary Examiner—F. L. Evans

[57] ABSTRACT

The invention relates to a spectral fluorometer arrangement including at least one laser light source, particularly for use in measuring the luminescence in the course of a qualitative and quantitative determination of a sample material, the region of which to be excited is arranged in the object point of an emission monochromator and spectrograph, respectively, a holographic grating of said monochromator being provided with a central opening for passage of the exciting laser beam, and beam directing means are provided outside of the plane of symmetry of said emission monochromator and spectrograph, respectively.

11 Claims, 5 Drawing Figures

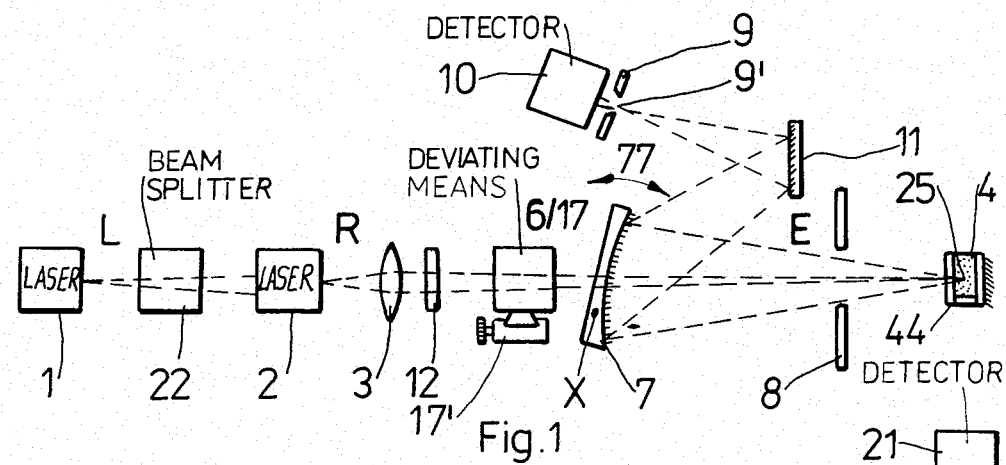
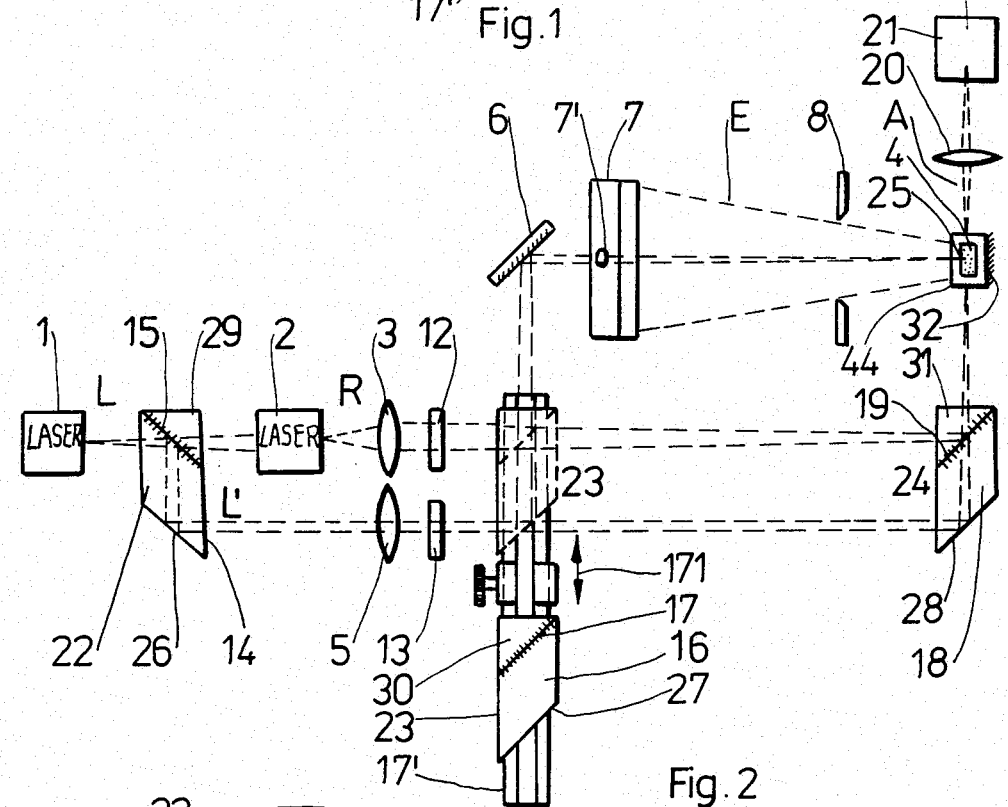
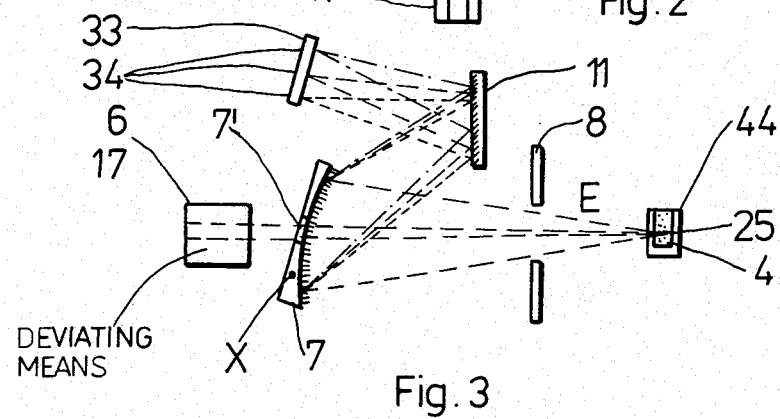

SPECTRALFLUOROMETER ARRANGEMENT

The invention relates to an improvement in a spectral fluorometer arrangement including a laser light-source, particularly for use in measuring the luminescence for a qualitative and quantitative determination of a sample material.

Luminescence measurements are of particular advantage when small quantities of sample materials are investigated with respect to their photophysical and photochemical properties of electronically excited atoms and molecules, respectively.

For luminescence measurements spectral fluorometers are used, where a radiation source of a considerably wide spectral continuum, such as a xenon lamp is imaged into the entry slit of an excitation monochromator.

The monochromatic light resulting in the exit slit is focused into a sample through a respective lens, thus exciting the sample material in the consequence of which a luminescence results.

The luminescent light is generally focused via further lenses into the entry slit of an emission monochromator, thereby including a right angle to the excitation light, a photodetector is arranged subsequent to the exit slit of the arrangement for evaluation of the radiation.

Such an arrangement is disadvantageous since light losses and stray light occurs due to the plurality of lenses employed for focussing luminescent light upon the entry slit.

The slit itself involves further losses, particularly when emission monochromators of high resolution are concerned and, hence, with small slit width losses occur due to blackout and stray light due to diffraction at the slit.

The effective opening ratio for the focussing of the luminescent light into the entry slit is limited by imaging aberrations.

In the course of measuring the sample material the latter is excited along the excitation light beam throughout the sample material, whereas when focussing the luminescent light into the entry slit of the emission monochromator the image of the excited sample material is produced and extends at right angles to the slit, which considerably reduces the efficiency of the device.

It is a further disadvantage that when considerably high absorbing sample material is investigated the path of beams has to be varied since the excitation of the sample material and the measuring of the luminescence has to be carried out from the same side.

The latter is also referred to as incident light measurements. It is an object of the present invention to obviate the above disadvantages.

It is a further object of the present invention to provide an arrangement for investigating sample materials which permits a measurement of the luminescence under incident light and under right angles considered between the exciting light and emitted light at a considerably high sensitivity and signal-to-background ratio of hitherto negligible amounts of luminescent substances.

It is a further object of the invention to provide a spectral fluorometer arrangement which considerably reduces the limitations of the sensitivity at a reduced number of optical elements for directing the luminescent radiation. These and other objects are realised in a spectral fluorometer arrangement including at least one laser light source and a tunable dyestuff laser being pumped by said laser light source, optical directing means for focussing the laser beam into a sample material and means for analysing the radiation emitted from said sample material excited by said dyestuff laser beam.

The arrangement further includes a beam splitter inserted into a path of beams between said laser light source and said dyestuff laser for splitting the light beam into a first and a second beam.

At least one lens and at least one grey wedge are inserted into said first and said second beam; furthermore, beam fusing means are provided in said first and said second beam in the vicinity of said sample material for positioning both beams in an equal position in the range of the sample to be excited.

The means for analysing the sample material are an emission monochromator and an emission spectrograph, respectively The range of the sample material to be excited is located in the object point of an emission monochromater and spectrograph, respectively, the latter is provided with an entry reflector and concave grating, respectively, which is provided with a central opening for passing the laser beam to the sample material. Further means for directing the laser beam are provided outside the plane of symmetry of the emission monochromator and spectrograph, respectively. The plane in which the laser beam impinges upon the object point after passing the deviating reflectors includes the entry axis of the emission monochromator and spectrograph, respectively, and is at right angles to the plane of symmetry of the emission monochromator and spectrograph, respectively.

The plane of symmetry of the emission monochromator and spectrograph, respectively, is the plane passing the center of the entry opening, the center of the entry reflector and concave grating, respectively and the center of the exit opening.

The entry axis of the emission monochromator and spectrograph, respectively, passes the center of the entry opening and the center of the entry reflector and of the concave grating, respectively.

Advantageously, a semiconductor photodetector is arranged at the place of a point which is conjugated to the object-point of the emission spectrograph, furthermore, the exit slit is arranged at the place of a point which is conjugated to the object point of the emission monochromator, whereas no entry slit is provided in the entry opening of the emission monochromator and spectrograph, respectively, provided that the laser light is sufficiently focussed in the sample material.

Since semiconductor photodetectors only have small light sensitive faces, the emission monochromator and spectrograph, respectively, require corrected holographic gratings of low astigmatism. For some applications the stray light portion in the emission monochromator and emission spectrograph, respectively, is still too high, or the spectral resolution too low. This to overcome, a further monochromator and spectrograph, respectively, is arranged subsequent to the exit slit under use of a concave grating in the emission monochromator and under imaging the zeroeth order or a higher order into the exit slit.

Advantageously, the subsequent monochromator and spectrograph, respectively, includes a concave grating having the same parameters as the concave grating of the emission monochromator. Both concave gratings are positioned for an operation in the same order.

The light from the concave grating of the emission monochromator is reversely imaged upon the concave grating of the subsequent monochromator and spectrograph, respectively. The exit slit of the emission monochromator is the entry slit of the subsequent monochromator and spectrograph, respectively.

The image of the zeroeth order in the entry slit of the subsequent monochromator and spectrograph, respectively is identical to the image of a concave reflector corresponding to the concave grating. When poorly absorbing samples are excited through the center of the entrance slit and the concave grating, respectively, means are provided to enhance the excitation of the sample material. Said means advantageously consist in silvering the back face of the sample material which reflects the exciting beam back in itself.

Figure 5:
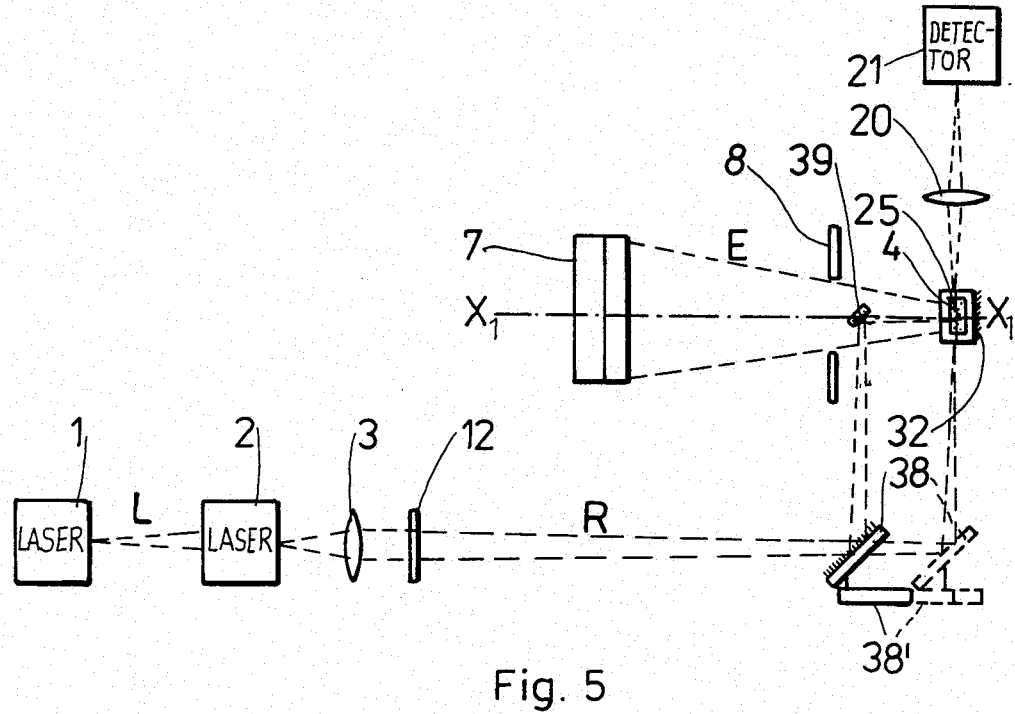

In order that the invention may be more readily understood reference is made to the accompanying drawings which illustrate diagrammatically and by way of example two embodiments thereof and where FIG. 1 is a schematical side view of a spectral fluorometer arrangement, FIG. 2 is a schematical top view of the spectral fluorometer arrangement of FIG. 1, and FIG. 3 a semiconductor detector line of the spectral fluorometer arrangement, FIG. 4 is a schematical side view of a fluorometer arrangement including two concave gratings, and FIG. 5 is a schematical top view of a further embodiment of a spectral fluorometer arrangement.

In FIG. 1 a laser light source 1, for example, a $N_2$-laser emits a beam L in which a beam splitting means 22 is inserted followed by a dyestuff laser 2, a collective lens 3, a grey wedge 12 and beam fusing and deviating means 6 and 17 which laterally displace the laser beam L and direct the beam L upon an object point 25 of a sample material 4 contained in a cell 44, having a silvered face 32 after passage through an opening 7' (FIG. 2) of a concave grating 7 of an emission monochromator and an aperture 8 for a luminescence light E. The deviating or beam fusing means 17 is mounted upon a displacement means 17' which permits displacement of the beam fusing and deviating means 17 along a direction indicated by a double arrow 171, the displacement direction being at right angles to the beams R and L' (FIG. 2) in a plane defined by the latter two beams.

A measuring arrangement for measuring the luminescence radiation E from the excited sample material 25 comprises the aperture 8, the holographic concave grating 7, which is tiltable about a pivot X in the directions indicated by a double arrow 77, a deviating reflector 11, an aperture 9 and a photodetector 10.

In operation, the laser light source 1 produces a laser beam L which is directed upon the beam splitter 22 which splits the laser beam L into a first portion and into a second portion L'.

About 10 percent of the radiation is coupled out of the laser beam L by the beam splitter 22.

The first portion pumps the tunable dyestuff laser 2 which emits a laser radiation R.

The latter is focussed by the collective lens 3 upon the sample 25 after passage through the grey wedge 12 and the deviating means 6 and 17 which laterally displace the laser radiation R, which passes the opening 7' in the center of the concave grating 7 which is part of an emission monochromator and after passage through the aperture 8 impinges upon a definite range 25 of the sample material 4 and excites the latter to emit the luminescence radiation E which, in reverse direction to the exciting radiation R and L', passes the aperture 8 and impinges upon the holographic grating 7. The aperture 8 and the grating 7 define an opening ratio of 1:3 for the indication of the luminescence. The holographic grating 7 is tiltable by not shown means about the point X and depending on the inclination of the grating 7 relative to the incident luminescence radiation the luminescence light of a definite wavelength is reflected at the grating 7 to the reflector 11 which directs the luminescence light upon the exit slit 9 of the detector 10.

The desired wavelength in the exit slit 9 is produced by tilting the grating 7 about the pivot point X in the direction indicated by the double arrow 77, thus a respective position of the object point 25 relative to the position of an image point 9' of the grating 7 in the exit slit 9 is adjusted, which ensures that the astigmatism in the exit slit 9 is low and the spectral resolution considerably high over a wide spectral range.

In FIG. 2 the fluorometer of FIG. 1 is shown in top view. The laser light source 1 produces the laser beam L which is split by a partially reflective layer 15 of the beam splitting means 22.

The latter is composed of a rhomboid 14 and a right angle prism 29, two parallel faces of said rhomboid 14 are substantially at right angles to the incident laser beam L, whereas the partially reflective layer 15 which is inclined relative to the beam L by substantially 45° is both the hypotenuse face of the right angle prism 29 and the one of the two other parallel faces of said rhomboid 14, the other face 26 of said two other parallel faces is a reflective one.

The laser beam L is split into a first portion which is transmitted through the face 15 and which pumps the dyestuff laser 2, and into a second portion which is deflected by said layer 15 and impinges upon the face 26 where it is again reflected and leaves the beam splitting means 22 in parallel but spaced relation to said first portion to be focused by a collective lens and a grey wedge 13 and deviated by a reflective face 27 of a beam fusing means 23 and the deviating reflector 6 upon object point 25 of the sample material 4.

The beam fusing means 23 is constituted in analogy to the beam splitting means 22 of a rhomboid 16 and a right angle prism 30 which are arranged in analogy, however, mirror symmetrical relation to the beam splitting means 22 in both, the second portion of the laser beam L and in the dyestuff laser radiation R.

Hence, the partially reflective layer 17 is transmissive to the laser radiation L' from the $N_2$-laser but reflective to the dyestuff laser radiation R. Thus, the second portion of the radiation L' and the radiation R are equally positioned after the layer 17.

The beam fusing means 23 is shown in dashed lines inserted into the beams L' and R to indicate that it is removable from out of the dashed lines position into the heavy line position by the displacement means 17', the directions of movement is indicated by the double arrow 171.

When the beam fusing means 23 is removed from out of the beams L and R, the laser beam R impinges upon a partially reflecting layer 19 which is inclined relative to the beam R by an angle of 45° and belongs to a beam fusing means 24 which is constituted in analogy to the beam fusing means 23 but positioned adjacent the sample material 4.

The dyestuff laser beam R is folded about 90° at said layer 19 and directed into the sample material 4. The partially reflecting layer 19 is reflective to the wavelengths of the dyestuff laser 2 and transmissive to the $N_2$-laser radiation L'.

The latter impinges upon a reflecting face 28 (in analogy to the face 27 of the beam fusing means 23) of the beam fusing means 24 and is reflected at right angles through the layer 19 to impinge upon the object point 25 of the sample material 4. After the layer 19 both radiations L and R are equally positioned.

The cell 44 is provided with the silvered rear face 32, which enhances the radiation R and L' when the beam fusing and deviating means 17 is inserted into the radiation R and L'.

The sample material 4 is excited at right angles to the measuring direction of the luminescence light emitted from the sample 4. In addition to the luminescence measurement of the radiation E an absorption measurement is feasible. The sample material emits a radiation A which passes a collective lens 20 arranged subsequent to the sample material 4 and is evaluated by a detector 21 arranged in the focus of the lens 20.

In FIG. 3 the spectral fluorometer arrangement shows the emission spectrograph including the beam fusing and deviating means 17, the grating 7 having a central opening 7, a pivot X, the aperture 8 for the luminescent radiation E, the deviating reflector 11 and a semiconductor photodetector line 33.

The substantially coinciding laser radiation L' and R is directed by the beam fusing and deviating means 17 through the opening 7' of the holographic grating 7 to impinge upon the object point 25 of the sample material 4. The latter is excited and the emitted luminescent radiation E is reflected at the corrected holographic grating 7, deviated at the reflector 11 and a luminescence spectrum is produced in a point 34 which is conjugated to the point 35. At the place of the luminescence spectrum 34 the semiconductor photodetector line 33 is arranged to detect the luminescence spectrum.

In FIG. 4 the arrangement of FIG. 3 is provided with an additional reflector 36 and an additional concave grating 37, a slit 40 and a slit 35.

The luminescence radiation E passes via the grating 7 and the reflector 11 the exit slit 40 of the emission monochromator. The reflector 11 is arranged at right angles to the radiation R and L', and in parallel, however, laterally displaced relation to the aperture 8.

After passing the exit slit 40 which serves further to reduce the stray light portions, the luminescent radiation is focused via the reflector 36 and the grating 37 into the exit slit 35.

When the grating 7 of the first monochromator images the zeroeth order into the slit 40, it is feasible to measure the entire spectrum by tilting the grating 37 about the pivoting point Y in the directions indicated by the double arrow 41. When the negative first order is imaged into the slit 40 the same wavelength is imaged into the exit slit 35 by synchronously tilting the grating 37. The latter has the same parameters as the grating 7 and is equally operated in the first negative order. In FIG. 5 the $N_2$-laser 1 emits a radiation L which pumps the dyestuff laser 2 to emit a radiation R which is directed through the lens 3 and varied in its intensity by the grey wedge 12 via a first deviating means 38 and a second deviating means 39 and focused upon the sample material 4 in the cell 44, having again a silvered rear face 32. The sample material is excited by the radiation R and emits the luminescent radiation E which has an axis $X_1—X_1$.

The second deviating means 39 has a comparatively small diameter and directs the exciting radiation upon the sample material 4 substantially in parallel to the axis $X_1—X_1$. By a displacement means 38' the first deviating means 38 are displaced substantially in parallel to the axis $X_1—X_1$ in a dashed line position so that the exciting radiation R is directed upon the sample material 4 at right angles to the axis $X_1—X_1$.

We claim:

1. A spectral fluorometer arrangement comprising in mutual optical alignment, at least one laser light source for emitting at least one laser beam,
   a cell for receiving a sample material to be analysed,
   an emission monochromator, including a first holographic grating
   and a detector,
   said monochromator having an object point,
   an entry slit and an exit slit,
   said holographic grating having a central opening,
   said monochromator having an optional axis passing the center of said central opening and the center of said sample material,
   first means for directing said laser beam upon said sample material through said opening of said holographic grating,
   said laser beam being for exciting said sample material,
   said sample material emitting a luminescence radiation,
   said luminescence radiation between said sample material and said grating being substantially in parallel to said axis,
   said sample material being located in said object point of said emission monochromator,
   second means for directing said luminescence radiation from said grating to said detector means,
   said entry slit being located adjacent said object point,
   said detector being for detecting said luminescence radiation.

2. An arrangement as claimed in claim 1, wherein said exit slit is located adjacent said detector.

3. An arrangement as claimed in claim 2, wherein said emission monochromator has an image point conjugate to said object point, said detector being located substantially in said image point.

4. An arrangement as claimed in claim 3, wherein the detector is a semiconductor photodetecting line.

5. An arrangement as claimed in claim 1, wherein said exit slit is located adjacent said second means for directing said luminescence radiation in the latter between said second means for directing and said detector means, and wherein a deviating means and a second holographic grating are subsequently arranged in the luminescence radiation between said exit slit and said detector.

6. An arrangement as claimed in claim 5, wherein said deviating means and said second holographic grating constitute a further monochromator.

7. An arrangement as claimed in claim 6, wherein said first holographic grating and said second holographic grating have the same parameters, said exit slit being the entry slit for said further monochromator, said first and said second holographic grating being positioned for an operation in equal order, the luminescence radiation being laterally reversed from said first holographic grating to said second holographic grating.

8. An arrangement as claimed in claim 7, wherein said cell has a silvered rear face.

9. A spectral fluorometer arrangement comprising in mutual optical alignment, at least one laser light source for emitting at least one laser beam, a cell for receiving a sample material to be analysed, an emission spectrograph, including a first holographic grating and a detector, said spectrograph having an object point, an entry slit and exit slit, said holographic grating having a central opening, said spectrograph having an optical axis passing the center of said central opening and the center of said sample material, first means for directing said laser beam upon said sample material through said opening of said holographic grating, said laser beam being for exciting said sample material, said sample material emitting a luminescence radiation, said luminescence radiation between said sample material and said grating being substantially in parallel to said axis, said sample material being located in said object point of said emission spectrograph, second means for directing said luminescence radiation from said grating to said detector means, said entry slit being located adjacent said object point, said detector being for detecting said luminescence radiation, said exit slit being located adjacent said detector.

10. An arrangement as claimed in claim 9, wherein said emission spectrograph has an image point conjugate to said object point, said detector being located substantially in said image point.

11. An arrangement as claimed in claim 10, wherein the detector is a semiconductor photodetecting line.

* * * * *